United States Patent
Ikawa et al.

(12)
(10) Patent No.: US 6,812,252 B2
(45) Date of Patent: Nov. 2, 2004

(54) ACYLSULFONAMIDE DERIVATIVES

(75) Inventors: Hiroshi Ikawa, Tokyo (JP); Masato Nishimura, Tokyo (JP); Keiji Okada, Tokyo (JP); Takashi Nakamura, Tokyo (JP); Kazuhiro Kojima, Tokyo (JP); Hideki Kosono, Kamakura (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/335,868

(22) Filed: Jan. 3, 2003

(65) Prior Publication Data
US 2003/0181764 A1 Sep. 25, 2003

Related U.S. Application Data

(63) Continuation of application No. PCT/JP01/05626, filed on Jun. 29, 2001.

(30) Foreign Application Priority Data
Jul. 5, 2000 (JP) .................................. 2000-204002

(51) Int. Cl.[7] ...................... A61K 31/18; C07C 311/32; C07C 311/37
(52) U.S. Cl. ..................... 514/603; 564/86; 564/88; 564/90; 564/92
(58) Field of Search ..................... 564/92, 86, 88, 564/90; 514/603

(56) References Cited

U.S. PATENT DOCUMENTS

| 6,555,584 B1 | 4/2003 | Ikawa et al. ............ 514/603 |
| 2003/0162818 A1 | 8/2003 | Ikawa et al. |
| 2003/0191323 A1 | 10/2003 | Ikawa et al. |

FOREIGN PATENT DOCUMENTS

| EP | 1 300 142 A1 | 4/2003 |
| JP | 11-171848 | 6/1999 |
| JP | 11-171856 | 6/1999 |
| JP | 11-222437 | 8/1999 |
| JP | 2000-38350 | 2/2000 |
| JP | 2001-48794 | 2/2001 |
| JP | 2001-199888 | 7/2001 |

OTHER PUBLICATIONS

Raffa, L., *Il Farmaco– Ed. Sc.*, vol. X11, 4, pp. 279–292 (1957).

Primary Examiner—Peter O'Sullivan
(74) Attorney, Agent, or Firm—Oblon, Spivak, McClelland, Maier & Neustadt, P.C.

(57) ABSTRACT

The present invention provides new acylsulfonamide derivatives such as 4-(3-trifluoromethyl)phenylethynyl-N-(2-(5-ketohexanoylamino)sulfonylphenyl)benzamide, 4-(3-trifluoromethyl)phenylethynyl-N-(2-(2-propyloxy-acetylamino)sulfonylphenyl)benzamide or analogues thereof. These acylsulfonamide derivatives have a hypoglycemic effect equal to or superior to the effects of the conventional hypoglycemic agents and they are free from the side effects unlike the glitazone compounds.

21 Claims, No Drawings

ACYLSULFONAMIDE DERIVATIVES

This application is a Continuation of International Application No. PCT/JP01/05626 Filed on Jun. 29,2001.

BACKGROUND OF THE INVENTION

The present invention relates to new acylsulfonamide derivatives, in particular, new acylsulfonamide derivatives having hypoglycemic effect.

Diabetes is a disease caused by various factors such as overeating, lack of exercise, stress and hereditary factors. The number of the patients suffering from diabetes is increasing as the life of the people is improved. At present, the number of diabetes cases is so large that this disease is called "a national disease" in Japan. Diabetes is classified into two types, i. e. insulin dependent diabetes mellitus (IDDM) and non-insulin dependent diabetes mellitus (NIDDM). In Japan, at least 90% of diabetes cases is NIDDM. Patients suffering from NIDDM scarcely have the subjective symptoms and when the patients are found to suffer from this disease, the disease has already progressed in many cases. In such a case, a suitable therapy is required for avoiding complications.

For the treatment of NIDDM, dietetic therapy or kinetotherapy is employed at first. By such a therapy, the effects such as reduction in obesity, increase in the insulin sensitivity and reduction of insulin requirement in peripheries and reduction of endogenous insulin requirement can be expected. As a result, the blood glucose level can be controlled. However, in many cases, a sufficient effect in reducing the blood glucose level cannot be obtained by the dietetic therapy or kinetotherapy. In such cases, the patients are treated with medicines.

Hypoglycemic agents known at present include insulin preparations, insulin secretion accelerators, α-glucosidase inhibitors, biguanide and glitazone compounds. Depending on the pathological conditions of the patients, a medicine is given alone or in combination with other medicines having different action mechanisms.

In the background of NIDDM onset, it is considered to be important to solve the obesity caused by excess in vivo energy due to overeating and lack of exercise and also insulin resistance induced thereby. In the above-described medicines, glitazone compounds, capable of reducing the blood glucose level by releasing the insulin resistance, attract the greatest attention.

Glitazone compounds induce the differentiation of fat cells by activating PPAR γ which is one of intranuclear receptors, and thus improve insulin resistance of peripheral tissues and exhibit the pharmaceutical effect. However, these compounds have strong side effects, and a serious hepatopathy including cases of death was reported. Further, because these compounds accelerate the differentiation of fat cells, the fat accumulation is accelerated to induce the obesity. Also in clinical cases, reduction or weakening of the pharmaceutical effect of them by the increase in the body weight or accumulation of fats was also reported.

DISCLOSURE OF THE INVENTION

The treatment with the above-described hypoglycemic agents is not yet satisfactory and, also the glitazone compounds which now attract the attention are also not yet perfect because of the above-described side effects. Under these circumstances, an object of the present invention is to develop a new compound having a hypoglycemic effect equal to or superior to the effects of the conventional medicines and free from the side effects unlike the glitazone compounds.

After intensive investigations, the inventors have found acylsulfonamide derivatives of general formula (I) given below. The present invention has been completed on the basis of this finding.

The present invention provides acylsulfonamide derivatives of the following general formula (I):

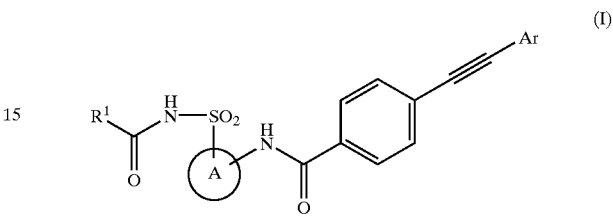

wherein Ar represents a phenyl group substituted with one or more fluorine atoms, trifluoromethyl groups or trifluoromethoxyl groups, $R^1$ represents a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted aromatic hydrocarbon group, a substituted or unsubstituted aromatic heterocyclic group, a substituted amino group, a substituted or unsubstituted $C_1$ to $C_{20}$ alkoxyl group, a substituted or unsubstituted $C_2$ to $C_{20}$ alkenyloxyl group, a substituted or unsubstituted $C_2$ to $C_{20}$ alkynyloxyl group or a group of the formula: $R^4O-$ wherein $R^4$ represents a substituted or unsubstituted aromatic hydrocarbon group or a substituted or unsubstituted aromatic heterocyclic group, and ring A represents a substituted or unsubstituted aromatic hydrocarbon group, a substituted or unsubstituted aromatic heterocyclic group or a substituted or unsubstituted cycloalkyl group.

DESCRIPTION OF THE PREFERRED EMBODIMENTS

The detailed description will be made on the acylsulfonamide derivatives of the present invention. In this specification, the term "$C_1$ to $C_{20}$ alkyl groups" includes linear, branched and cyclic groups such as methyl, ethyl, n-propyl, 1-methylethyl, cyclopropyl, n-butyl, 2-methylpropyl, 1-methylproyl, 1,1-dimethylethyl, cyclobutyl, n-pentyl, 1-methylbutyl, 2-methylbutyl, 3-methylbutyl, cyclopentyl, 2,2-dimethylpropyl, n-hexyl, 1-methylpentyl, 2-methylpentyl, 4-methylpentyl, 1-ethylbutyl, 2-ethylbutyl, 3,3-dimethylbutyl, cyclohexyl, n-heptyl, 1-methylhexyl, 2-methylhexyl, 5-methylhexyl, 4,4-dimethylpentyl, 1-propylbutyl, 2-ethylpentyl, cyclohexylmethyl, 1,1-diethylpropyl, cycloheptyl, n-octyl, 1-methylheptyl, 6-methylheptyl, 1-ethylhexyl, 2-ethylhexyl, 2-cyclohexylethyl, 5,5-dimethylhexyl, cyclooctyl, n-nonyl, 1-methyloctyl, 7-methyloctyl, 6,6-dimethylheptyl, n-decyl, 1-methylnonyl, 8-methylnonyl, 7,7-dimethyloctyl, n-undecyl, 1-methyldecyl, 9-methyldecyl, 8,8-dimethylnonyl, n-dodecyl, 1-methylundecyl, 10-methylundecyl, 5-methylundecyl, 9,9-dimethyldecyl, dodecyl, tetradecyl, pentadecyl, hexadecyl, heptadecyl, octadecyl, nonadecyl and eicosyl groups. These alkyl groups may have various substituents. Examples of the substituents include halogen atoms such as chlorine, bromine, iodine and fluorine atoms, nitro group, amino group, cyano group, hydroxyl group, alkoxyl groups, thiol group, oxo group, trichloromethyl group, trifluoromethyl group, aromatic hydrocarbon groups such as phenyl and naphthyl groups, and aromatic heterocyclic groups such as thienyl, furyl and pyridyl groups. These aromatic hydrocarbon groups and aromatic heterocyclic groups may further have substituents such as halogen atoms, alkyl groups, alkoxyl groups, nitro group, amino group, cyano group, hydroxyl group and thiol group.

The "$C_2$ to $C_{20}$ alkenyl groups" may be linear or branched groups. They include, for example, 1-methyl-1-propenyl, 1-methyl-2-propenyl, 2-methyl-2-propenyl, ethenyl, 1-methylethenyl, 1-propenyl, 2-propenyl, 1-butenyl, 2-butenyl, 2-pentenyl, 1-pentenyl, 3-methylbutenyl, 1,3-butanedienyl, 1-hexenyl, 2-hexenyl, 3,3-dimethyl-1-butenyl, 4,4-dimethyl-1-pentenyl, 1,3-pentanedienyl, 1,3-hexanedienyl, 2-cyclohexylethenyl, octenyl, nonenyl, decenyl, undecenyl, dodecenyl, tridecenyl, tridecadienyl, tetradecenyl, tetradecadienyl, pentadecenyl, pentadecadienyl, pentadecatrienyl, hexadecenyl, hexadecadienyl, hexadecatrienyl, heptadecenyl, heptadecadienyl, heptadecatrienyl, octadecenyl, octadecadienyl, octadecatrienyl, nonadecenyl, nonadecadienyl, nonadecatrienyl, eicosenyl, eicosadienyl and eicosatrienyl groups. These alkenyl groups may further have various substituents. Examples of them may be the same as those listed above as the substituents of the $C_1$ to $C_{12}$ alkyl groups.

The "$C_2$ to $C_{20}$ alkynyl groups" may be linear or branched groups. They include, for example, 1-propynyl, 2-propynyl, 1-methyl-2-propynyl, 1-ethyl-2-propynyl, ethynyl, 1-butynyl, 2-butynyl, 1,3-butadiynyl, 1-pentynyl, 2-pentynyl, 1,3-pentadiynyl, 1-hexynyl, 2-hexynyl, 1,3-hexadiynyl, tridecynyl, tridecadiynyl, tetradecynyl, tetradecadiynyl, pentadecynyl, pentadecadiynyl, pentadecatriynyl, hexadecynyl, hexadecadiynyl, hexadecatriynyl, heptadecynyl, heptadecadiynyl, heptadecatriynyl, octadecynyl, octadecadiynyl, octadecatriynyl, nonadecynyl, nonadecadiynyl, nonadecatriynyl, eicosynyl, eicosadiynyl and eicosatriynyl groups. These alkynyl groups may have various substituents. Examples of them may be the same as those listed above as the substituents of the $C_1$ to $C_{12}$ alkyl groups.

The term "substituted or unsubstituted aromatic hydrocarbon groups" indicates monocyclic or polycyclic aromatic hydrocarbon groups which may have one or more of various substituents on the ring. They include, for example, phenyl, methylphenyl, dimethylphenyl, methoxyphenyl, dimethoxyphenyl, nitrophenyl, dinitrophenyl, chlorophenyl, dichlorophenyl, bromophenyl, dibromophenyl, iodophenyl, fluorophenyl, trifluoromethylphenyl, aminophenyl, hydroxyphenyl, mercaptophenyl, α-naphthyl and β-naphthyl groups.

The term "substituted or unsubstituted aromatic heterocyclic groups" indicates those having a five-membered ring or six-membered ring containing at least one hetero atom such as nitrogen atom, sulfur atom or oxygen atom. These groups may be condensed with benzene ring and have one or more substituents on the ring. They include, for example, pyridyl, furyl, thienyl, indolyl, quinolyl, isoquinolyl, benzofuranyl, benzothienyl, imidazolyl, benzimidazolyl, thiazolyl, oxazolyl, pyrazolyl, pyrimidyl, pyrazinyl, isoxazolyl, isoindolyl and pyrrolyl groups.

The "substituted amino groups" are amino groups wherein the nitrogen atom is substituted with one or two of the above-described, substituted or unsubstituted $C_1$ to $C_{20}$ alkyl groups, substituted or unsubstituted $C_2$ to $C_{20}$ alkenyl groups, substituted or unsubstituted $C_2$ to $C_{20}$ alkynyl groups, substituted or unsubstituted aromatic hydrocarbon groups or substituted or unsubstituted aromatic heterocyclic groups. The alkyl group may form a 5- to 7-membered saturated heterocycle which may contain nitrogen atom, oxygen atom or sulfur atom together with the nitrogen atom to which the alkyl group is bonded. The substituted amino groups include, for example, methylamino, ethylamino, propylamino, butylamino, pentylamino, hexylamino, dimethylamino, diethylamino, dipropylamino, 2-propenylamino, 2-butenylamino, 3-butenylamino, 1-pyrrolidinyl, piperidino, 1-piperazinyl, morpholino, thiomorpholino, perhydroazepinyl, phenylamino, naphthylamino, pyridylamino, furylamino and thienylamino group.

The term "$C_1$ to $C_{20}$ alkoxyl groups" indicates alkyl-substituted oxy groups in which the alkyl groups are as defined above. Examples of these groups are methoxyl, ethoxyl, n-propoxyl, 1-methylethoxyl, n-butoxyl, 2-methylpropoxyl, 1-methylpropoxyl, 2-methyl-2-propoxyl, n-pentyloxyl, 3-methylbutoxyl, n-hexyloxyl, 4-methylpentoxyl, n-pentyloxyl, n-octyloxyl, n-nonyloxyl, n-decyloxyl, n-undecyloxyl, tridecyloxyl, tetradecyloxyl, pentadecyloxyl, hexadecyloxyl, heptadecyloxyl, octadecyloxyl, nonadecyloxyl and eicosyloxyl groups. These alkoxyl groups may further have various substituents. Examples of them may be the same as those listed above as the substituents of the $C_1$ to $C_{12}$ alkyl groups.

The ring represented by A in the acylsulfonamide derivatives of the above general formula (I) provided by the present invention is the above-described aromatic hydrocarbon group or aromatic heterocyclic group. As for the substitution mode of these groups, it is desirable that the acylsulfonamide side chain and the amide side chain have their substitution sites at the 1,2-position, or at the 1,1-position when A is a cycloalkyl group.

The following compounds can be exemplified as the acylsulfonamide derivatives of the present invention:

4-(3-Trifluoromethyl)phenylethynyl-N-(2-hexanoylaminosulfonylphenyl)benzamide;

4-(3-trifluoromethyl)phenylethynyl-N-(2-(5-ketohexanoylamino)sulfonylphenyl)benzamide;

4-(3-trifluoromethyl)phenylethynyl-N-(2-(2-propyloxyacetylamino)sulfonylphenyl)benzamide;

4-(4-trifluoromethyl)phenylethynyl-N-(2-hexanoylaminosulfonylphenyl)benzamide;

4-(4-trifluoromethoxy)phenylethynyl-N-(2-hexanoylaminosulfonylphenyl)benzamide;

4-(4-trifluoromethoxy)phenylethynyl-N-(2-(5-ketohexanoylamino)sulfonylphenyl)benzamide;

4-(4-fluoro)phenylethynyl-N-(2-hexanoylamino-sulfonylphenyl)benzamide;

4-(4-fluoro)phenylethynyl-N-(2-(5-ketohexanoylamino)sulfonylphenyl)benzamide; and 4-(3-fluoro)phenylethynyl-N-(2-hexanoylamino-sulfonylphenyl)benzamide.

The acylsulfonamide derivatives of the present invention can be produced by, for example, a method shown by the following chemical scheme:

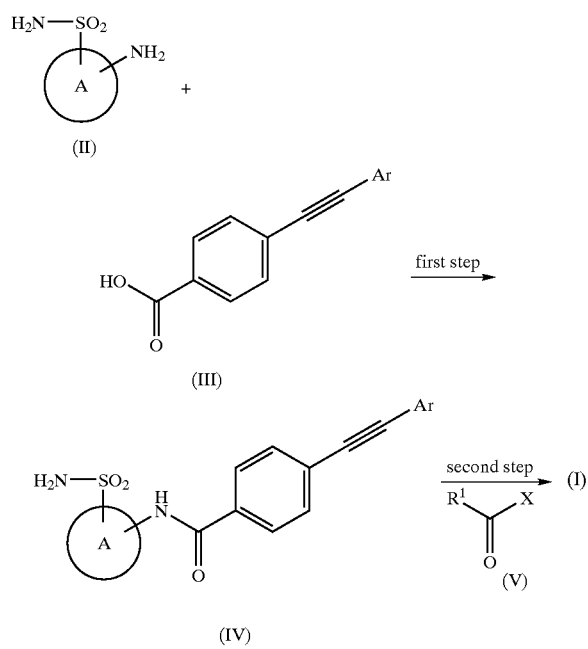

wherein R¹, Ar and ring A are as defined above, and X represents a halogen atom such as chlorine or bromine atom, succinimido group or imidazolyl group.

The First Step

In this step, an aminosulfonamide compound of formula (II) is condensed with a carboxylic acid of formula (III) to form a sulfonamide compound of formula (IV).

The condensation in this step can be carried out by a process wherein a condensing agent such as carbonyldiimidazole, dicyclohexylcarbodiimide or 1-ethyl-3-(3-dimethylaminopropyl) carbodiimide hydrochloride is used; a process wherein a carboxylic acid of formula (III) is converted into a corresponding acid halide with a halogenating agent such as thionyl chloride or phosphorus pentachloride and condensing it in the presence of an appropriate base; or a process wherein a carboxylic acid of formula (III) is converted into an acid anhydride with p-toluenesulfonyl chloride, ethyl chlorocarbonate, pivaloyl chloride or the like and then the acid anhydride is condensed in the presence of an appropriate base.

In carrying out the reaction, it is desirable that the aminosulfonamide compound of formula (II) and the carboxylic acid of formula (III) are used in almost equimolar amounts. Although the reaction temperature and the reaction time are not generally limited because they vary depending on the kind of the compounds, the intended compound can be obtained in a high yield by carrying out the reaction at a temperature ranging from about 0° C. to around the boiling point of the solvent used for about 0.1 to 25 hours. The amount of the condensing agent is preferably about 1.2 equivalents per equivalent of the carboxylic acid of formula (III) to be reacted.

The bases usable herein include alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkali metal alkoxides such as sodium methoxide, sodium ethoxide, potassium methoxide and potassium tert-butoxide; trialkylamines such as trimethylamine and triethylamine; and organic bases and inorganic bases such as pyridine, dimethylaminopyridine, picoline and lutidine. The base is used in an amount of 1 to 10 equivalents per equivalent of the carboxylic acid compound.

In this step, the reaction can be carried out in an inert solvent. The solvents include ethers such as diethyl ether, tetrahydrofuran and dioxane; aromatic hydrocarbons such as benzene, toluene and xylene; hydrocarbons such as cyclopentane and cyclohexane; halogenated hydrocarbons such as dichloromethane, dichloroethane, trichloroethane and chloroform; nitriles such as acetonitrile and propionitrile; esters such as ethyl acetate; N,N-dimethylformamide and dimethyl sulfoxide; and mixtures of them with water.

The Second Step

In this step, a sulfonamide compound of formula (IV) is reacted with an acyl compound of formula (V) in the presence of a base to produce an acylsulfonamide compound of formula (I).

In formula (V) for the acyl compounds used in this step, X represents a halogen atom such as chlorine or bromine atom, succinimido group or imidazolyl group.

The bases usable in step 2 are the same as those usable in step 1. The amount of the base is preferably 1 to 10 equivalents per equivalent of the carboxylic acid compound.

For the reaction, the sulfonamide compound of formula (IV) and the acyl compound of formula (V) are preferably used in nearly equimolar amounts. Although the reaction temperature and the reaction time are not generally limited because they vary depending on the kind of the compounds, the intended compound can be obtained in a high yield by carrying out the reaction at a temperature ranging from about 0° C. to around the boiling point of the solvent for about 0.1 to 25 hours.

The reaction can be carried out in an inert solvent. The inert solvents may be the same as those in step 1.

The intended acylsulfonamide derivatives of the above general formula (I) can be obtained by suitably combining the above-described reactions. If necessary, the reaction solution can be purified by an ordinary purification means such as filtration, decantation, extraction, washing, distillation of the solvent, column chromatography, thin-layer chromatography, recrystallization or distillation.

When the acylsulfonamide derivative of above general formula (I) of the present invention is administered as a medicine to human beings, the effective dose thereof varies depending on the symptoms and age of the patient. For example, 5 to 30 mg/day of the active ingredient is preferably orally administered once or dividedly into three portions a day.

The hypoglycemic agent of the present invention can be orally administered in various dosage forms such as tablets, capsules, granules, a powder, troches and a liquid. These preparations can be produced by methods known per se. For example, a compound of the general formula (I) of the present invention is suitably combined with a filler such as starch, mannitol or lactose; a binder such as sodium carboxymethylcellulose or hydroxypropylcellulose; a disintegrator such as crystalline cellulose or carboxymethylcellulose; a lubricant such as talc or magnesium stearate; and/or a fluidizing agent such as light anhydrous silicic acid to form tablets, capsules, granules, a powder, troches, etc.

The hypoglycemic agent of the present invention can be in the form of an injection. The injection can be prepared by previously dispersing or dissolving the hypoglycemic agent in an aqueous carrier such as physiological saline with a surfactant or a dispersing agent, or the hypoglycemic agent can be kept in the form of a crystalline preparation for injection or freeze-dried preparation which can be dispersed or dissolved each time for the injection. The aqueous carrier may contain a pH regulator or a stabilizing agent, if necessary.

The dose and route of administration of the injection are not particularly limited A safe and necessary amount of the injection can be given by the intravenous, intraarterial, subcutaneous or intraperitoneal injection at once or intravenous drip infusion.

EXAMPLES

The following Reference Examples and Examples will further illustrate the present invention, which by no means limit the invention.

Reference Example 1

4-(3-Trifluoromethyl)phenylethynyl-N-(2-sulfamoylphenyl)benzamide

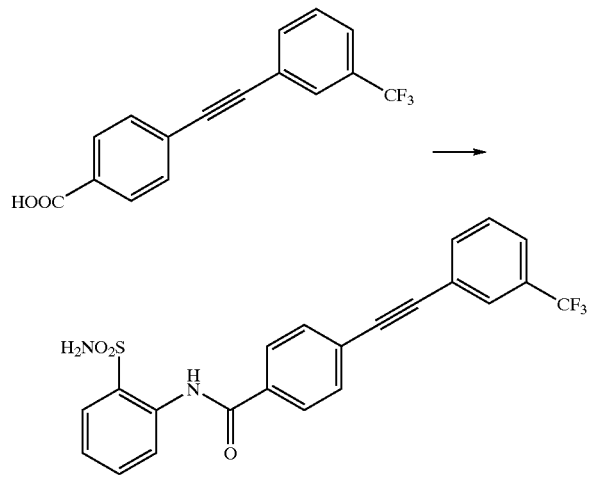

A solution of 2.90 g (10.0 mmol) of 4-(3-trifluoromethyl) phenylethynylbenzoic acid and 2 ml of thionyl chloride in benzene (30 ml) was heated under reflux for 2 hours and then the solvent was evaporated. The residue was dissolved in methylene chloride (30 ml). The obtained solution was added dropwise to a solution of 1.72 g (10.00 mmol) of 2-aminobenzenesulfonamide in pyridine (50 ml) under cooling with ice. After stirring at room temperature for 18 hours, methylene chloride was evaporated under reduced pressure. The residue was dissolved in ethyl acetate, and the obtained solution was washed with 1 N aqueous hydrochloric acid solution, water and saturated aqueous sodium chloride solution in that order. After drying over anhydrous sodium sulfate, the solvent was evaporated under reduced pressure. The residue was recrystallized from ethyl acetate—hexane to obtain 3.34 g (yield: 75.3%) of the title compound.

$^1$H-NMR (δ, DMSO-$d_6$): 7.34–7.40 (1H, m), 7.65–7.74 (2H, m), 7.76–7.86 (4H, m), 7.91–7.96 (2H, m), 7.98–8.02 (3H, m), 8.42–8.46 (1H, m), 10.42 (1H, br-s)

Example 1

4-(3-Trifluoromethyl)phenylethynyl-N-(2-hexanoylaminosulfonylphenyl)benzamide

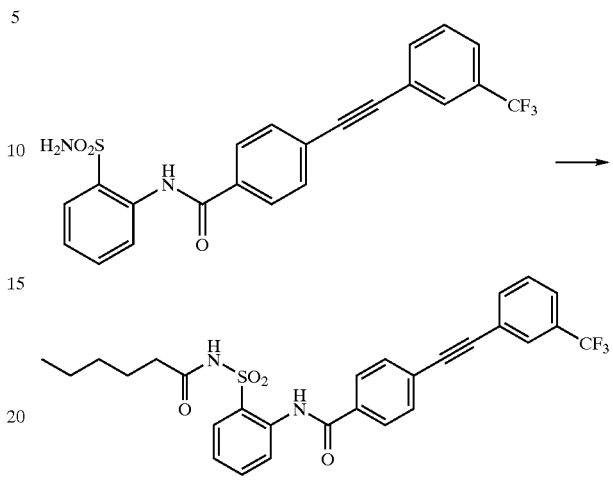

0.16 ml (1.10 mmol) of hexanoyl chloride was added to a solution of 444 mg (1.0 mmol) of 4-(3-trifluoromethyl) phenylethynyl-N-(2-sulfamoylphenyl)benzamide and 244 mg (2.0 mmol) of 4-dimethylaminopyridine in THF (35 ml). The resulting mixture was stirred at room temperature for 18 hours and then THF was evaporated under reduced pressure. The residue was dissolved in ethyl acetate, and the obtained solution was washed with 1 N aqueous hydrochloric acid solution, water and saturated aqueous sodium chloride solution in that order. After drying over anhydrous sodium sulfate, the solvent was evaporated under reduced pressure. The residue was purified by the silica gel column chromatography to obtain 504 mg (yield: 92.8%) of the title compound.

$^1$H-NMR (δ, DMSO-$d_6$): 0.77 (3H, t, J=7 Hz), 1.04–1.22 (4H, m), 1.36–1.45 (2H, m), 2.22 (2H, t, J=7 Hz), 7.39–7.46 (1H, m), 7.69–7.73 (1H, m), 7.73–7.80 (1H, m), 7.80–7.86 (3H, m), 7.90–8.00 (3H, m), 8.04 (2H, d, J=8 Hz), 8.36–8.40 (1H, m), 11.48 (1H, s), 12.51 (1H, s

IR (v, KBr): 3384, 3116, 1718, 1660, 1544, 1510, 1442, 1340, 1170, 1130, 758, 698, 586

EI MS (m/z, %): 542 (m+, 26), 444 (5), 428 (2), 364 (37), 273 (100), 245 (12)

m.p.: 194–196° C.

Example 2

4-(3-Trifluoromethyl)phenylethynyl-N-(2-(5-ketohexanoylamino)-sulfonylphenyl)benzamide

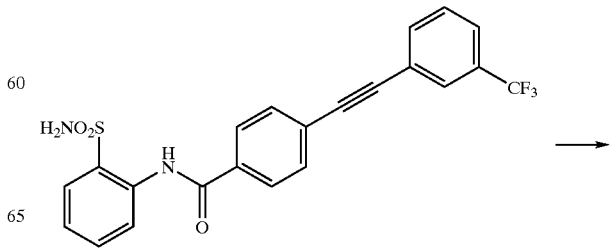

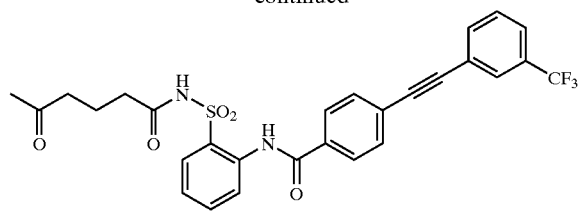

143 mg (1.1 mmol) of 5-ketohexanoic acid was added to a solution of 444 mg (1.0 mmol) of 4-(3-trifluoromethyl) phenylethynyl-N-(2-sulfamoylphenyl)benzamide and 403 mg (3.3 mmol) of 4-dimethylaminopyridine in THF (35 ml). 210 mg (1.1 mmol) of tosyl chloride was slowly added to the resulting mixture. The obtained mixture was stirred at room temperature for 3 hours and then THF was evaporated under reduced pressure. The residue was dissolved in ethyl acetate and then the obtained solution was washed with 1 N aqueous hydrochloric acid solution, water and saturated sodium chloride solution in that order. After drying over anhydrous sodium sulfate, the solvent was evaporated under reduced pressure. The residue was purified by the silica gel column chromatography to obtain 520 mg (yield: 93.4%) of the title compound.

$^1$H-NMR (δ, CDCl$_3$): 1.75–1.82 (2H, m), 2.09 (3H, s), 2.26 (2H, t, J 7 Hz), 2.44 (2H, t, J=7 Hz), 7.24–7.29 (1H, m), 7.50 (1H, t, J=7 Hz), 7.60–7.73 (5H, m), 7.82 (1H, d, J=1 Hz), 8.00 (1H, dd, J=8, 1 Hz), 8.03–8.06 (2H, m), 8.70 (1H, dd, J=7, 1 Hz), 9.22 (1H, s), 10.49 (1H, s)

IR (v, KBr): 1716, 1704, 1688, 1588, 1438, 1340, 1296, 1126, 760, 696, 590

FABMS (m/z, %): 555 (m−H, 100)

m.p.: 169–171° C.

Example 3
4-(3-Trifluoromethyl)phenylethynyl-N-(2-(2-propyloxyacetylamino)sulfonylphenyl)benzamide

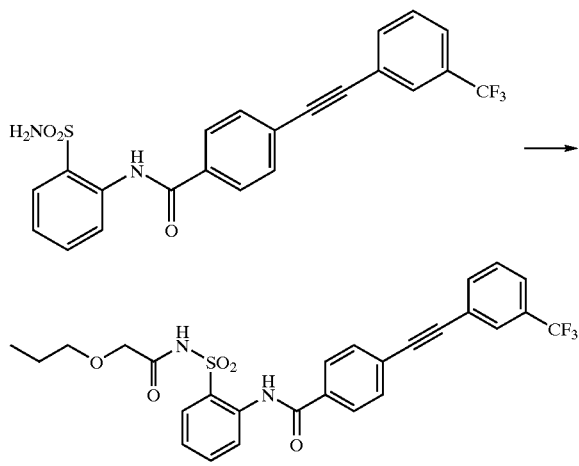

130 mg (1.1 mmol) of 2-propyloxyacetic acid was added to a solution of 444 mg (1.0 mmol) of 4-(3-trifluoromethyl) phenylethynyl-N-(2-sulfamoylphenyl)benzamide and 403 mg (3.3 mmol) of 4-dimethylaminopyridine in THF (35 ml). 210 mg (1.1 mmol) of tosyl chloride was slowly added to the resulting mixture. The obtained mixture was stirred at room temperature for 3 hours and then THF was evaporated under reduced pressure. The residue was dissolved in ethyl acetate and then the obtained solution was washed with 1 N aqueous hydrochloric acid solution, water and saturated sodium chloride solution in that order. After drying over anhydrous sodium sulfate, the solvent was evaporated under reduced pressure. The residue was purified by the silica gel column chromatography to obtain 496 mg (yield: 91.0%) of the title compound.

$^1$H-NMR (δ, CDCl$_3$): 0.91 (3H, t, J=7 Hz), 1.55–1.63 (2H, m), 3.45 (2H, t, J=7 Hz), 3.94 (2H, s), 7.26–7.31 (1H, m), 7.51 (1H, t J=8 Hz), 7.60–7.74 (5H, m), 7.82 (1H, s), 8.02–8.08 (3H, m), 8.75 (1H, dd, J=8, 1 Hz), 9.03 (1H, s), 10.50 (1H, s)

IR (v, KBr): 3412, 3284, 1724, 1692, 1590, 1342, 1154, 854, 766

FABMS (m/z, %): 543 (m−H, 100)

m.p.: 175–177° C.

Reference Example 2
4-(4-Trifluoromethyl)phenylethynyl-N-(2-sulfamoylphenyl)benzamide

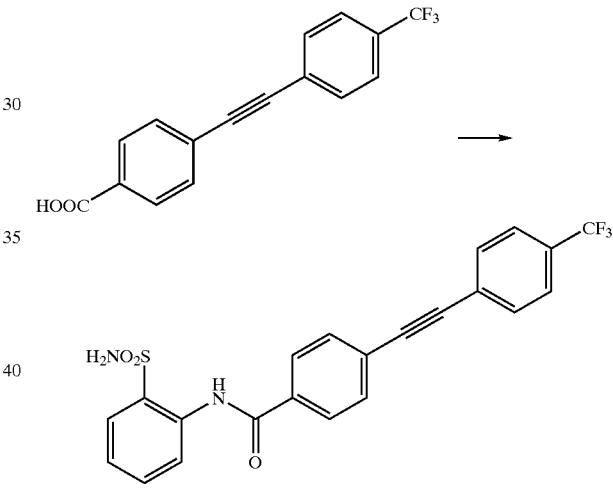

A solution of 2.90 g (10.0 mmol) of 4-(4-trifluoromethyl) phenylethynylbenzoic acid and 2 ml of thionyl chloride in benzene (30 ml) was heated under reflux for 2 hours and then the solvent was evaporated under reduced pressure. The residue was dissolved in methylene chloride (30 ml). The obtained solution was added dropwise to a solution of 1.72 g (10.00 mmol) of 2-aminobenzenesulfonamide in pyridine (50 ml) under cooling with ice. After stirring at room temperature for 18 hours, methylene chloride was evaporated under reduced pressure. The residue was dissolved in ethyl acetate, and the obtained solution was washed with 1 N aqueous hydrochloric acid solution, water and saturated aqueous sodium chloride solution in that order. After drying over anhydrous sodium sulfate, the solvent was evaporated under reduced pressure. The residue was recrystallized from ethyl acetate—hexane to obtain 3.52 g (yield: 79.3%) of the title compound.

$^1$H-NMR (δ, DMSO-d$_6$): 7.34–7.40 (1H, m), 7.65–7.70 (1H, m), 7.78 (2H, s), 7.81–7.87 (6H, m), 7.92 (1H, dd, J=8, 1 Hz), 7.99 (2H, d, J=8 Hz), 8.44 (1H, dd, J=8, 1 Hz)

Example 4

4-(4-Trifluoromethyl)phenylethynyl-N-(2-hexanoylaminosulfonylphenyl)benzamide

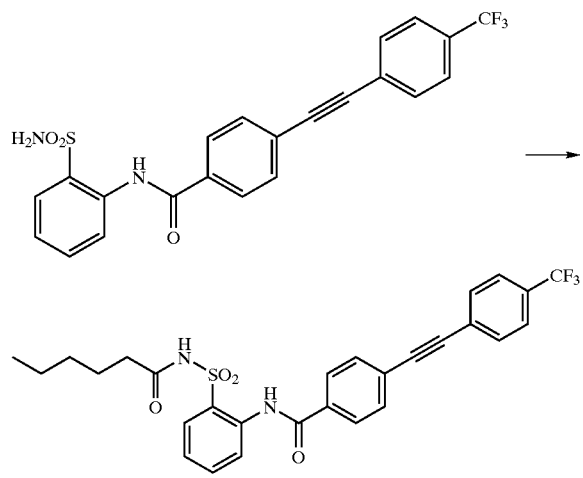

0.16 ml (1.10 mmol) of hexanoyl chloride was added to a solution of 444 mg (1.0 mmol) of 4-(4-trifluoromethyl)phenylethynyl-N-(2-sulfamoylphenyl)benzamide and 244 mg (2.0 mmol) of 4-dimethylaminopyridine in THF (35 ml). The obtained mixture was stirred at room temperature for 18 hours and then THF was evaporated under reduced pressure. The residue was dissolved in ethyl acetate and then the obtained solution was washed with 1 N aqueous hydrochloric acid solution, water and saturated sodium chloride solution in that order. After drying over anhydrous sodium sulfate, the solvent was evaporated under reduced pressure. The residue was purified by the silica gel column chromatography to obtain 513 mg (yield: 94.6%) of the title compound.

$^1$H-NMR (δ, DMSO-$d_6$): 0.77 (3H, t, J=7 Hz), 1.04–1.22 (4H, m), 1.36–1.45 (2H, m), 2.22 (2H, t, J 7 Hz), 7.40–7.47 (1H, m), 7.74–7.80 (1H, m), 7.80–7.98 (6H, m), 7.96 (1H, dd, J 8, 1 Hz), 8.04 (2H, d, J=8 Hz), 8.36–8.41 (1H,), 10.48 (1H, s), 12.52 (1H, s)

IR (ν, KBr): 3116, 1700, 1648, 1582, 1534, 1318, 1166, 1134, 844

EI MS (m/z, %): 542 (m+, 34), 444 (6), 428 (3), 364 (50), 273 (100), 245 (20) p m. p.; 210–212° C.

Reference Example 3

4-(4-Trifluoromethoxyl)phenylethynyl-N-(2-sulfamoylphenyl)benzamide

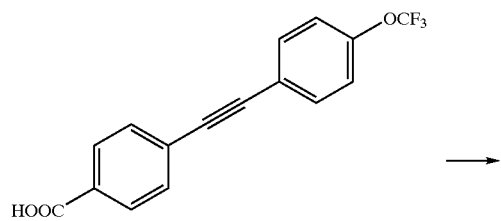

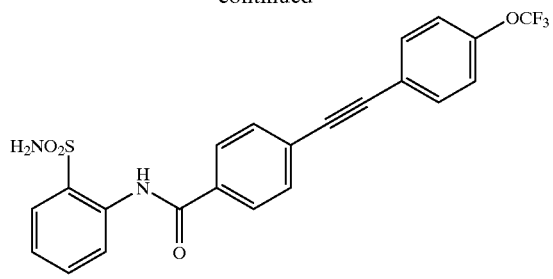

A solution of 3.06 g (100 mmol) of 4-(4-trifluoromethoxy)phenylethynylbenzoic acid and 2 ml of thionyl chloride in benzene (30 ml) was heated under reflux for 2 hours and then the solvent was evaporated under reduced pressure. The residue was dissolved in methylene chloride (30 ml). The obtained solution was added dropwise to a solution of 1.72 g (10.00 mmol) of 2-aminobenzenesulfonamide in pyridine (50 ml) under cooling with ice. After stirring at room temperature for 18 hours, methylene chloride was evaporated under reduced pressure. The residue was dissolved in ethyl acetate, and the obtained solution was washed with 1 N aqueous hydrochloric acid solution, water and saturated sodium chloride solution in that order. After drying over anhydrous sodium sulfate, the solvent was evaporated under reduced pressure. The residue was recrystallized from ethyl acetate—hexane to obtain 3.32 g (yield: 72.1%) of the title compound.

$^1$H-NMR (δ, CDCl$_3$): 4.85–5.10 (2H, br-s), 7.20–7.24 (2H, m), 7.25–7.30 (1H, m), 7.58–7.62 (3H, m), 7.64 (2H, d, J=8 Hz), 7.95 (2H, d, J=8 Hz), 7.98 (1H, dd, J=8, 1 Hz), 8.56 (1H, dd, J 8, 1 Hz), 10.13 (1H, s

Example 5

4-(4-Trifluoromethoxy)phenylethynyl-N-(2-hexanoylaminosulfonylphenyl)benzamide

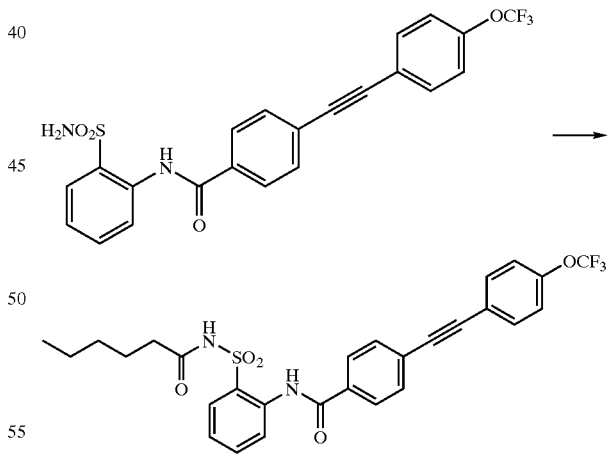

0.16 ml (1.10 mmol) of hexanoyl chloride was added to a solution of 460 g (1.0 mmol) of 4-(4-trifluoromethoxy)phenylethynyl-N-(2-sulfamoylphenyl)benzamide and 244 mg (2.0 mmol) of 4-dimethylaminopyridine in THF (35 ml). The obtained mixture was stirred at room temperature for 18 hours and then THF was evaporated under reduced pressure. The residue was dissolved in ethyl acetate and then the obtained solution was washed with 1 N aqueous hydrochloric acid solution, water and saturated sodium chloride solution in that order. After drying over anhydrous sodium sulfate, the solvent was evaporated under reduced pressure. The residue was purified by the silica gel column chromatography to obtain 517 mg (yield: 95.7%) of the title compound.

¹H-NMR (δ, DMSO-d₆) 0.77 (3H, t, J=7 Hz), 1.03–1.22 (4H, m), 1.36–1.44 (2H, m), 2.22 (2H, t, J=7 Hz), 7.40–7.46 (1H, m), 7.47 (2H, d, J 8 Hz), 7.75 (2H, d, J 8 Hz), 7.75 (2H, d, J 8 Hz), 7.80 (2H, d, J=8 Hz), 7.95 (1H, dd, J=8, 1 Hz), 8.03 (2H, d, J=8 Hz), 8.38–8.41 (1H, m), 10.47 (1H, s), 12.51 (1H, s)

IR (ν, KBr): 3112, 1700, 1650, 1582, 1516, 1250, 1166, 858

EI MS (m/z, %): 558 (m+, 22), 460 (3), 380 (18), 289 (100), 261 (17)

m.p.: 197–199° C.

Example 6

4-(4-Trifluoromethoxy)phenylethynyl-N-(2-(5-ketohexanoylamino)-sulfonylphenyl)benzamide

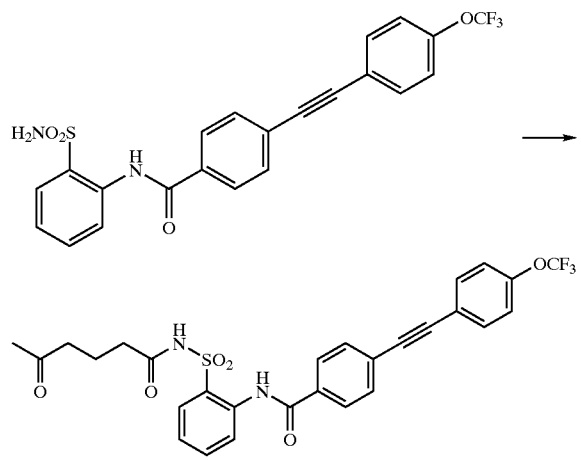

143 mg (1.1 mmol) of 5-ketohexanoic acid was added to a solution of 460 mg (1.0 mmol) of 4-(4-trifluoromethoxy)phenylethynyl-N-(2-sulfamoylphenyl)benzamide and 403 mg (3.3 mmol) of 4-dimethylaminopyridine in THF (35 ml). 210 mg (1.1 mmol) of tosyl chloride was slowly added to the resulting mixture. The obtained mixture was stirred at room temperature for 3 hours and then THF was evaporated under reduced pressure. The residue was dissolved in ethyl acetate and then the obtained solution was washed with 1 N aqueous hydrochloric acid solution, water and saturated sodium chloride solution in that order. After drying over anhydrous sodium sulfate, the solvent was evaporated under reduced pressure. The residue was purified by the silica gel column chromatography to obtain 538 mg (yield: 94.0%) of the title compound.

1H-NMR (δ, CDCl₃): 1.75–1.82 (2H, m), 2.09 (3H, s), 2.27 (2H, t, J 7 Hz), 2.46 (2H, t, J=7 Hz), 7.21–7.30 (5H, m), 7.56–7.71 (3H, m), 8.01–8.06 (3H, m), 8.72 (1H, dd, J=8, 1 Hz), 9.07 (1H, s), 10.46 (1H, s)

IR (ν, KBr): 3320, 1736, 1716, 1652, 1582, 1538, 1516, 1444, 1250, 1136, 856, 764, 576

FABMS (m/z, %): 571 (m–H, 18), 459 (100)

m.p: 204–205° C.

Reference Example 4

4-(4-Trifluoro)phenylethynyl-N-(2-sulfamoylphenyl)benzamide

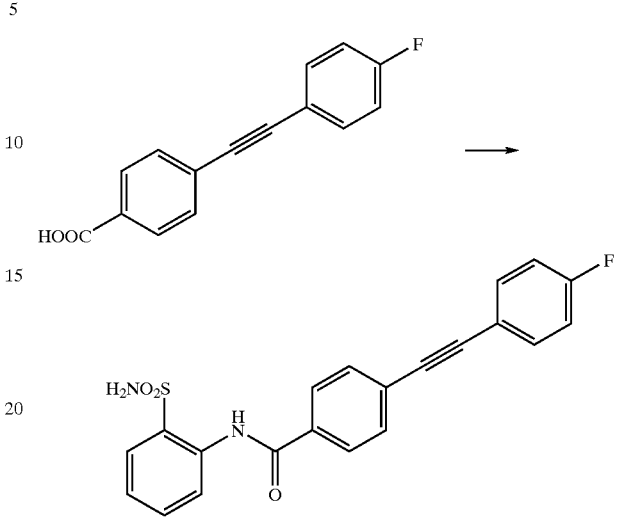

A solution of 2.40 g (10.0 mmol) of 4-(4-fluoro)phenylethynylbenzoic acid and 2 ml of thionyl chloride in benzene (30 ml) was heated under reflux for 2 hours and then the solvent was evaporated under reduced pressure. The residue was dissolved in methylene chloride (30 ml). The obtained solution was added dropwise to a solution of 1.72 g (10.00 mmol) of 2-aminobenzenesulfonamide in pyridine (50 ml) under cooling with ice. After stirring at room temperature for 18 hours, methylene chloride was evaporated under reduced pressure. The residue was dissolved in ethyl acetate, and the obtained solution was washed with 1 N aqueous hydrochloric acid solution, water and saturated sodium chloride solution in that order. After drying over anhydrous sodium sulfate, the solvent was evaporated under reduced pressure. The residue was recrystallized from ethyl acetate—hexane to obtain 3.08 g (yield: 78.2%) of the title compound.

¹H-NMR (δ, DMSO-d₆) 7.29–7.38 (3H, m), 7.65–7.70 (3H, m), 7.76–7.78 (4H, m), 7.92 (1H, dd, J 8 Hz, 1 Hz), 7.91 (1H, dd, J=8, 1 Hz), 7.96 (2H, d, J 8 Hz), 8.44 (1H, d, J=7 Hz), 10.42 (1H, br-s)

Example 7

4-(4-Fluoro)phenylethynyl-N-(2-hexanoylaminosulfonyl-phenyl)benzamide:

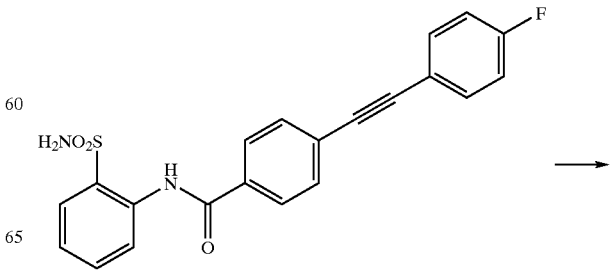

-continued

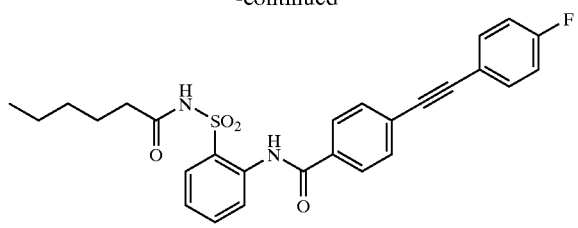

0.16 ml (1.10 mmol) of hexanoyl chloride was added to a solution of 394 g (1.0 mmol) of 4-(4-fluoro)phenylethynyl-N-(2-sulfamoylphenyl)benzamide and 244 mg (2.0 mmol) of 4-dimethylaminopyridine in THF (35 ml). The obtained mixture was stirred at room temperature for 18 hours and then THF was evaporated under reduced pressure. The residue was dissolved in ethyl acetate and then the obtained solution was washed with 1 N aqueous hydrochloric acid solution, water and saturated sodium chloride solution in that order. After drying over anhydrous sodium sulfate, the solvent was evaporated under reduced pressure. The residue was purified by the silica gel column chromatography to obtain 471 mg (yield: 95.7%) of the title compound.

$^1$H-NMR (δ, DMSO-$d_6$): 0.77 (3H, t, J=7 Hz), 1.08–1.12 (2H, m), 1.12–1.20 (2H, m), 1.38–1.42 (2H, m), 2.22 (2H, t, J 7 Hz), 7.30–7.35 (2H, m), 7.42 (1H, d t, J 7, 1 Hz), 7.66–7.71 (1H, m), 7.74–7.90 (3H, m), 7.95 (1H, dd, J=8, 1 Hz), 8.01 (2H, d, J=8 Hz), 8.38 (2H, d, J=8 Hz), 10.47 (1H, s), 12.52 (1H, br-s)

IR (ν, KBr) 3372, 1706, 1658, 1588, 1540, 1516, 1320, 834, 766

EI MS (m/z, %): 492 (m+, 26), 394 (6), 378 (3), 314 (25), 223 (100), 194 (15)

m.p.: 183–186° C.

Example 8
4-(4-Fluoro)phenylethynyl-N-(2-(5-ketohexanoylamino)sulfonylphenyl)benzamide

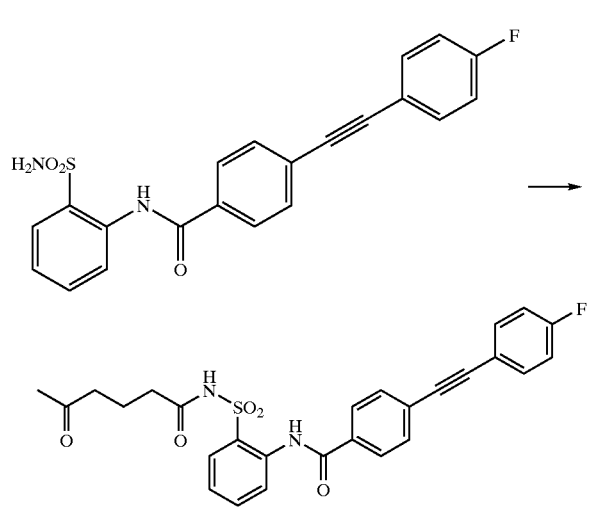

143 mg (1.1 mmol) of 5-ketohexanoic acid was added to a solution of 394 mg (1.0 mmol) of 4-(4-fluoro)phenylethynyl-N-(2-sulfamoylphenyl)benzamide and 403 mg (3.3 mmol) of 4-dimethylaminopyridine in THF (35 ml). 210 mg (1.1 mmol) of tosyl chloride was slowly added to the resulting mixture. After stirring at room temperature for 3 hours, THF was evaporated under reduced pressure. The residue was dissolved in ethyl acetate and then the obtained solution was washed with 1 N aqueous hydrochloric acid solution, water and saturated sodium chloride solution in that order. After drying over anhydrous sodium sulfate, the solvent was evaporated under reduced pressure. The residue was purified by the silica gel column chromatography to obtain 472 mg (yield: 93.1%) of the title compound.

$^1$H-NMR (δ, DMSO-$d_6$): 1.55–1.63 (2H, m), 2.00 (3H, s), 2.23 (2H, t, J=7 Hz), 2.31 (2H, t, J=7 Hz), 7.32 (2H, d, J=8 Hz), 7.43 (1H, t, J=7 Hz), 7.66–7.70 (2H, m), 7.76–7.78 (3H, m), 7.96 (1H, d, J=7 Hz), 8.01 (2H, d, J=8 Hz), 8.35 (1H, d, J=8 Hz), 10.44 (1H, s 12.52 (1H, s)

IR (ν, KBr): 1722, 1698, 1680, 1514, 1294, 854, 758, 584

FABMS (m/z, %): 505 (m−H, 90), 393 (100)

m.p.: 179–181° C.

Reference Example 5

4-(3-Fluoro)phenylethynyl-N-(2-sulfamoylphenyl)benzamide

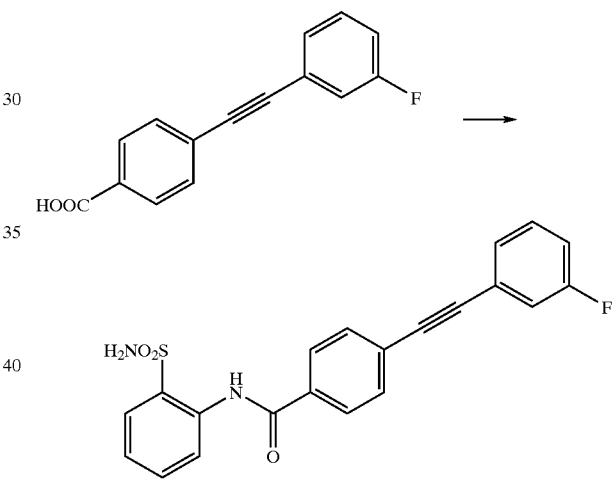

A solution of 2.40 g (10.0 mmol) of 4-(3-fluoro)phenylethynylbenzoic acid and 2 ml of thionyl chloride in benzene (30 ml) was heated under reflux for 2 hours and then the solvent was evaporated under reduced pressure. The residue was dissolved in methylene chloride (30 ml). The obtained solution was added dropwise to a solution of 1.72 g (10.00 mmol) of 2-aminobenzenesulfonamide in pyridine (50 ml) under cooling with ice. After stirring at room temperature for 18 hours, methylene chloride was evaporated under reduced pressure. The residue was dissolved in ethyl acetate, and the obtained solution was washed with 1 N aqueous hydrochloric acid solution, water and saturated sodium chloride solution in that order. After drying over anhydrous sodium sulfate, the solvent was evaporated under reduced pressure. The residue was recrystallized from ethyl acetate—hexane to obtain 3.06 g (yield: 77.7%) of the title compound.

$^1$H-NMR (δ, DMSO-$d_6$): 7.30–7.40 (2H, m), 7.45–7.54 (3H, m), 7.65–7.70 (1H, m), 7.76–7.82 (4H, m), 7.93 (1H, dd, J=8, 1 Hz), 7.79 (2H, d, J=8 Hz), 8.44 (1H, dd, J=8, 1 Hz)

Example 9

4-(3-Fluoro)phenylethynyl-N-(2-hexanoylaminosulfonyl-phenyl)benzamide

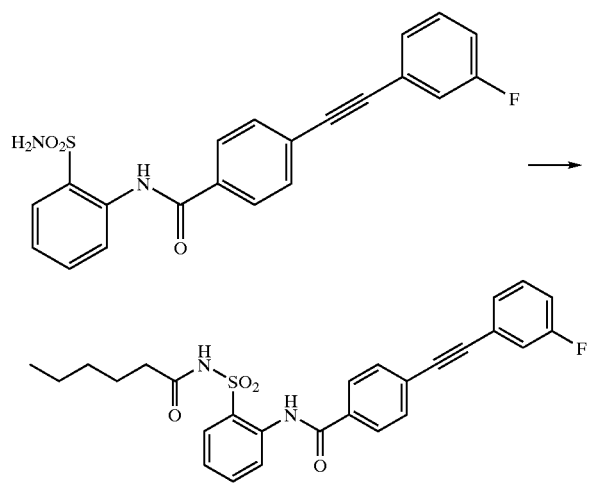

0.16 ml (1.10 mmol) of hexanoyl chloride was added to a solution of 394 g (10 mmol) of 4-(3-fluoro)phenylethynyl-N-(2-sulfamoylphenyl)benzamide and 244 mg (2.0 mmol) of 4-dimethylaminopyridine in THF (35 ml). After stirring at room temperature for 18 hours, THF was evaporated under reduced pressure. The residue was dissolved in ethyl acetate and then the obtained solution was washed with 1 N aqueous hydrochloric acid solution, water and saturated sodium chloride solution in that order. After drying over anhydrous sodium sulfate, the solvent was evaporated under reduced pressure. The residue was purified by the silica gel column chromatography to obtain 466 mg (yield: 94.6%) of the title compound.

$^1$H-NMR ($\delta$, DMSO-$d_6$): 0.77 (3H, t, J=7 Hz), 1.03–1.22 (4H, m), 1.35–1.45 (2H, m), 2.22 (2H, t, J=7 Hz), 7.30–7.36 (1H, m), 7.40–7.55 (4H, m), 7.74–7.82 (3H, m), 7.95 (1H, dd, J=8, 1 Hz), 8.03 (2H, d, J=8 Hz), 8.36–8.41 (1H, m), 10.47 (1H, s), 12.51 (1H, s)

IR (v, KBr): 1706, 1658, 1588, 1540, 1342, 1142, 862, 768, 584

EI MS (m/z, %): 492 (m+, 21), 394 (4), 378 (2), 314 (22), 223 (100), 194 (20)

m.p.: 183–186° C.

Test Example 1

Effect of Accelerating the Glucose Uptake in Cultured Skeletal Muscle Cells

Method

Rat skeletal muscle cell strain "L6 cells" in a confluent state were cultured in DME medium containing 2% of fetal calf serum for one week to differentiate into myotubes. The medium was replaced with the DME medium containing a compound synthesized in each of the above Examples. After culturing overnight followed by the thorough washing with HEPES buffer solution, an HEPES buffer solution containing 37 kBq/ml of 10 $\mu$M [3H]-2-deoxyglucose (2DG) was added thereto. After the culture at 37° C. for 10 minutes, the radioactivity of 2DG transmigrated into the cells was determined. The effect (%) of each compound on 2DG uptake was determined as compared with that in the control group.

The results are shown in Table 1.

TABLE 1

| Example | Effect of accelerating the glucose uptake (%) at 10 $\mu$M |
|---|---|
| 1 | 246 |
| 4 | 204 |
| 7 | 240 |
| 9 | 279 |

Test Example 2

Hypoglycemic Effect on Non-insulin-dependent Diabetes Model Mice (KK Mice)

Method

A compound (30 mg/kg) was administered to non-insulin-dependent diabetes model mice (8 weeks old) twice a day for one week. After final administration, the mice were fasted overnight and then the blood glucose concentration of each mouse was determined.

The hypoglycemic effect of the compound was calculated on the basis of the blood glucose level (100) in the control group. The results are shown in Table 2.

TABLE 2

| Example | Hypoglycemic effect (%) |
|---|---|
| 1 | 51.1 |
| 2 | 65.7 |
| 3 | 60.9 |
| 4 | 34.5 |
| 5 | 28.2 |
| 6 | 40.2 |
| 7 | 27.7 |
| 8 | 30.5 |
| 9 | 9.2 |

The acylsulfonamide derivatives of the present invention have a hypoglycemic effect equal to or superior to the effects of the conventional hypoglycemic agents and they are free from the side effects of the glitazone compounds now expected to be effective for the treatment. Thus, the acylsulfonamide derivatives of the invention are very useful as the active ingredient of hypoglycemic agents.

What is claimed is:

1. An acylsulfonamide compound of the following formula:

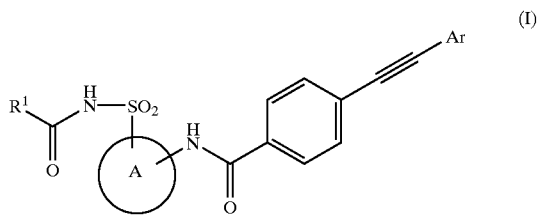

(I)

wherein Ar represents a phenyl group substituted with one or more fluorine atoms, trifluoromethyl groups or trifluoromethoxyl groups, $R^1$ represents a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted aromatic hydrocarbon group, a substituted or unsubstituted aromatic heterocyclic group, a substituted amino group, a substituted or unsubstituted $C_1$ to $C_{20}$ alkoxyl group, a substituted or unsubstituted $C_2$ to $C_{20}$ alkynyl group, a substituted or unsubstituted $C_2$ to $C_{20}$ alkynyloxyl group or a group of the formula: $R^4O-$ wherein $R^4$ represents a substituted or unsubstituted aromatic hydrocarbon group or a substituted or unsubstituted aromatic heterocyclic group, and ring A represents a substituted or unsubstituted aromatic hydrocarbon group, a substituted or unsubstituted aromatic heterocyclic group or a substituted or unsubstituted cycloalkyl group.

2. The acylsulfonamide compound according to claim 1, wherein the ring A is an aromatic hydrocarbon group having substitution sites at the 1,2-position, an aromatic heterocyclic group having substitution sites at the 1,2-position or a cycloalkyl group having substitution sites at the 1,1-position.

3. The acylsulfonamide compound according to claim 1, wherein $R^1$ represents a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted aromatic hydrocarbon group or a substituted or unsubstituted aromatic heterocyclic group.

4. The acylsulfonamide compound according to claim 2, wherein $R^1$ represents a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted aromatic hydrocarbon group or a substituted or unsubstituted aromatic heterocyclic group.

5. The acylsulfonamide compound according to claim 2, wherein $R^1$ represents a substituted or unsubstituted $C_1$ to $C_{20}$ alkyl group.

6. The acylsulfonamide compound according to claim 2, wherein $R^1$ represents a group represented by the formula: $-(CH_2)_4-CH_3$.

7. The acylsulfonamide compound according to claim 2, wherein $R^1$ represents a group represented by the formula: $-(CH_2)_3-CO-CH_3$.

8. The acylsulfonamide compound according to claim 2, wherein $R^1$ represents a group represented by the formula: $-(CH_2)-O-(CH_2)_2-CH_3$.

9. The acylsulfonamide compound according to claim 1, wherein Ar represents:

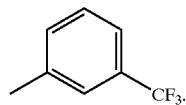

10. The acylsulfonamide compound according to claim 2, wherein Ar represents:

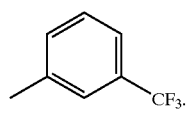

11. The acylsulfonamide compound according to claim 1, wherein Ar represents:

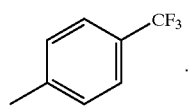

12. The acylsulfonamide compound according to claim 2, wherein Ar represents:

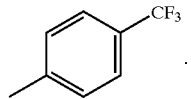

13. The acylsulfonamide compound according to claim 1, wherein Ar represents:

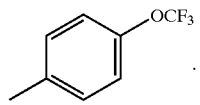

14. The acylsulfonamide compound according to claim 2, wherein Ar represents:

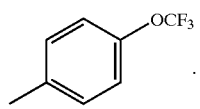

15. The acylsulfonamide compound according to claim 1, wherein the ring A is a phenyl group having substitution sites at the 1,2-positions.

16. The acylsulfonamide compound according to claim 15, wherein $R^1$ represents a group represented by the formula: $-(CH_2)_4-CH_3$.

17. The acylsulfonamide compound according to claim 15, wherein $R_1$ represents a group represented by the formula: $-(CH_2)_3-CO-CH_3$.

18. The acylsulfonamide compound according to claim 15, wherein $R^1$ represents a group represented by the formula: $-(CH_2)-O-(CH_2)_2-CH_3$.

19. The acylsulfonamide compound according to claim 15, wherein Ar represents:

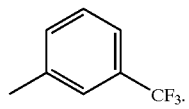

20. The acylsulfonamide compound according to claim 15, wherein Ar represents:

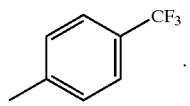

21. The acylsulfonamide compound according to claim 15, wherein Ar represents:

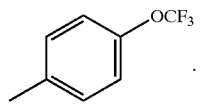

* * * * *